(12) United States Patent
Dupont et al.

(10) Patent No.: US 7,615,750 B2
(45) Date of Patent: Nov. 10, 2009

(54) DEVICE FOR DETERMINING THE SURFACE CONDITION OF A ROADWAY

(75) Inventors: Cedric Dupont, San Francisco, CA (US); Arne Stoschek, Palo Alto, CA (US); Jan MuEnchhoff, Gaimersheim (DE)

(73) Assignee: Volkswagen AG, Wolfsburg (DE)

( * ) Notice: Subject to any disclaimer, the term of this patent is extended or adjusted under 35 U.S.C. 154(b) by 451 days.

(21) Appl. No.: 11/221,603

(22) Filed: Sep. 8, 2005

(65) Prior Publication Data

US 2006/0076495 A1   Apr. 13, 2006

Related U.S. Application Data

(60) Provisional application No. 60/608,319, filed on Sep. 9, 2004.

(51) Int. Cl.
G01N 21/55 (2006.01)

(52) U.S. Cl. ............................ 250/339.11; 250/339.01; 250/339.06

(58) Field of Classification Search ............ 250/339.01, 250/339.06, 339.11
See application file for complete search history.

(56) References Cited

U.S. PATENT DOCUMENTS

| | | | |
|---|---|---|---|
| 4,651,290 A | * | 3/1987 | Masaki et al. ............... 701/80 |
| 4,690,553 A | * | 9/1987 | Fukamizu et al. ............. 356/51 |
| 5,218,206 A | * | 6/1993 | Schmitt et al. ......... 250/339.11 |
| 5,938,707 A | * | 8/1999 | Uehara ........................ 701/41 |
| 5,962,853 A | * | 10/1999 | Huth-Fehre et al. .... 250/339.11 |
| 2004/0130442 A1 | * | 7/2004 | Breed et al. ................. 340/443 |

FOREIGN PATENT DOCUMENTS

| | | | |
|---|---|---|---|
| DE | 27 12 199 B1 | | 9/1978 |
| DE | 41 33 359 A1 | | 4/1993 |
| DE | 42 35 104 A1 | | 4/1994 |
| DE | 4235104 A1 | * | 4/1994 |

OTHER PUBLICATIONS

International Search Report from EP 05 01 8740 (5 pages), Dec. 22, 2005.

* cited by examiner

*Primary Examiner*—Constantine Hannaher
*Assistant Examiner*—Casey Bryant
(74) *Attorney, Agent, or Firm*—King & Spalding L.L.P.

(57) ABSTRACT

A device for determination of the surface condition of a roadway includes a light-sensitive sensor to measure a light signal reflected from the surface of the roadway and an analyzer to determine the surface condition of the roadway as a function of the power of the light signal at a first wavelength in the infrared range, at a second wavelength in the infrared range and at least a third wavelength in the infrared range.

24 Claims, 5 Drawing Sheets

DEVICE FOR DETERMINING THE SURFACE CONDITION OF A ROADWAY

CROSS-REFERENCE TO RELATED APPLICATIONS

This application claims the benefit of U.S. Provisional Application No. 60/608,319 filed Sep. 9, 2004, the contents of which are hereby incorporated by reference in their entirety.

TECHNICAL FIELD

The invention concerns a device for determination of the surface condition of a roadway.

BACKGROUND

This type of device is known, for example, from U.S. Pat. No. 5,497,100.

A radar arrangement for street condition recognition in a vehicle is known from WO 98/48296, in which a transmitting-receiving antenna arrangement has an antenna diagram narrowly bundled in the horizontal and vertical direction, which illuminates a roadway section ahead of the vehicle within a distance range between 10 m and 100 m in the travel direction, and in which receiving devices receive echo signals from the illuminated roadway section and derive from them a classification of the roadway condition in the roadway section into stipulated street condition categories. The echo signals are then subdivided in the distance regions and evaluated.

A device for roadway condition recognition in a vehicle is known from WO 01/04659, in which the device for roadway condition recognition illuminates a roadway section ahead of the vehicle within a distance range between 2 m and 200 m in the travel direction and records echo signals, by means of receiving devices, from the illuminated roadway section, in order to derive from them a classification of the roadway condition in the roadway section into stipulated condition categories, in which a millimeter wave radar, having an intended diagram narrowly bundled in the horizontal and vertical direction is combined with an infrared laser radar, in which the millimeter wave radar and the infrared laser radar are aligned on the same roadway section, and in which the millimeter wave radar and the infrared laser radar are connected to a common evaluation unit.

EP 0 470 506 B1 discloses a sensor system for recognition of the surface condition on a roadway, in which an infrared sensor and receiver is formed with filters and linked for combined operation with a microwave transmitter and receiver, in which signals of the infrared or microwave receiver are processed by logic networks and linked to each other via one or more gates, in which condition displays are formed at the output of the gate and the logic network or at the output of the gates, in which, by means of an XOR gate, the individual state displays are checked for their logic condition correctness, and the result, in turn, is displayed via its own condition display.

The task of the invention is to provide an improved device for determination of the surface condition of a roadway.

SUMMARY

The aforementioned task is solved by a device for determination of the surface condition of a roadway, in which the device includes a light-sensitive sensor for measurement of a light signal reflected from the surface of a roadway and an analyzer to determine the surface condition of the roadway as a function of the power of the light signal at a first wavelength in the infrared range, at a second wavelength in the infrared range and at least a third wavelength in the infrared range.

In one embodiment of the invention, the surface condition of the roadway can be determined, by means of the analyzer, as a function of the ratio of power of the light signal of the first wavelength to the power of the light signal of the second wavelength, as a function of the ratio of the power of the light signal of the first wavelength to the power of the light signal of the third wavelength, and/or as a function of the ratio of the power of the light signal of the third wavelength to the power of the light signal of the second wavelength. This determination can additionally, or as an alternative, occur to determine the surface condition of the roadway as a function of the power of the light signal at the first wavelength in the infrared range not placed in a ratio, at the second wavelength in the infrared range and/or at the third wavelength in the infrared range.

The surface condition of the roadway can therefore be determined by means of the analyzer, for example, as a function of the ratio of the power of the light signal of the first wavelength to the power of the light signal of the second wavelength as a function of the power of the light signal at the first wavelength in the infrared range (not placed in a ratio), at the second wavelength of the infrared range and at the third wavelength in the infrared range. The surface condition of the roadway can be determined by means of the analyzer, for example, also in another embodiment of the invention as a function of the ratio of the power of the light signal of the first wavelength to the power of the light signal of the second wavelength, as a function of the ratio of the power of the light signal of the first wavelength to the power of the light signal of the third wavelength, and as a function of the ratio of the power of the light signal of the third wavelength to the power of the light signal of the second wavelength, as well as a function of the power of the light signal at the first wavelength in the infrared range not placed in a ratio, at the second wavelength in the infrared range and at the third wavelength in the infrared range.

In another embodiment of the invention, the first wavelength lies in a range between 950 nm and 850 nm. In another embodiment of the invention, the second wavelength lies in a range between 900 nm and 800 nm. In another embodiment of the invention, the third wavelength lies in a range between 850 nm and 750 nm.

In another embodiment of the invention, the surface condition of the roadway can be determined, by means of the analyzer, as a function of the ratio of power of the light signal at less than ten different wavelengths.

The aforementioned task is also solved by a vehicle with the aforementioned device for determination of the surface condition of a roadway, in which, by means of a light-sensitive sensor, the light signal reflected at a distance (adjustable as a function of the speed of the vehicle) in front of the vehicle from the surface of the roadway can be measured.

The aforementioned task is also solved by a vehicle with the aforementioned device for determination of the surface condition of the roadway, in which, by means of the light-sensitive sensor, the light signal reflected from the surface of the roadway as distance in front of the vehicle (proportional to the speed of the vehicle) can be measured.

The aforementioned task is also solved by a device for determination of the surface condition of a roadway, in which the device includes a light-sensitive sensor for measurement of a light signal reflected from the surface of the roadway and an analyzer to determine the surface condition of the roadway as a function of the power of the light signal at a first wavelength in the infrared range and/or at least a second wavelength in the infrared range, as well as a function of the ratio of the power of the light signal at the first wavelength and the power of the light signal at the second wavelength.

In an embodiment of the invention, the first wavelength lies in a range between 950 nm and 800 nm. In another embodiment of the invention, the second wavelength lies in a range between 900 nm and 750 nm.

In another embodiment of the invention, the surface condition of the roadway can be determined by the analyzer as a function of the ratio of the power of the light signal at less than ten different wavelengths.

The aforementioned task is also solved by a vehicle with the aforementioned device for determination of the surface condition of the roadway. The aforementioned task is also solved by a vehicle with the aforementioned device for determination of the surface condition of the roadway, in which, by means of the light-sensitive sensor, the light signal reflected from the surface of the roadway at a distance in front of the vehicle (adjustable as a function of the speed of the vehicle) can be measured.

The aforementioned task is also solved by a vehicle with the aforementioned device for determination of the surface condition of a roadway, in which, by means of the light-sensitive sensor, the light signal reflected from the surface of the roadway at a distance in front of the vehicle (adjustable proportional to the speed of the vehicle) can be measured.

The aforementioned task is also solved by the vehicle with a light-sensitive sensor for measurement of a light signal reflected from a roadway surface at a distance in front of the vehicle, adjustable as a function of the speed of the vehicle, and with an analyzer to determine the surface condition of the roadway as a function of the power of the light signal.

In one embodiment, the distance is adjustable in proportion to the speed of the vehicle.

The aforementioned task is also solved by a transport system, in which the transport system includes a first vehicle with a device for determination of the surface condition of a roadway and with a transmitter to transmit information concerning the surface condition of the roadway, and at least a second vehicle with a receiver to receive the information concerning the surface condition of the roadway. The device for determination of the surface condition of the roadway is then configured, in particular, according to an aforementioned device for determination of the surface condition of the roadway.

In one embodiment, the second vehicle also includes a device, especially comprising the aforementioned features, for determination of the surface condition of the roadway or a transmitter to transmit information concerning the surface condition of the roadway.

In another embodiment, the first vehicle also includes a receiver to receive the information transmitted from the second vehicle concerning the surface condition of the roadway.

In another embodiment, the second vehicle also includes a display to display the surface condition of the roadway.

The vehicle according to the invention is especially a land vehicle, usable individually in street traffic. Vehicles according to the invention are not particularly restricted to land vehicles with an internal combustion engine.

The roadway according to the invention is especially a paved street, but is not restricted to paved streets.

The condition of a roadway surface according to the invention can be a roadway condition, a street condition or a surface condition of a roadway. The surface condition of a roadway according to the invention can be a roughness and/or a "material", for example, ice, water on asphalt or a dry street surface.

A wavelength according to the claims is not necessary restricted to a single wavelength. A wavelength according to the claims can also include a narrow range of wavelengths that can be passed through an appropriate optical filter or can be generated by an appropriate light source. How narrow this range is supposed to be is guided according to the embodiments of appropriate optical filters of lights sources. The range, however, should be interpreted as narrowly as possible.

Power of a signal according to the invention is supposed to include equivalents, like the amplitude of the signal, its amount, its square or the like.

Additional advantages and details are apparent from the following description of practical examples:

DETAILED DESCRIPTION

Figure 1:
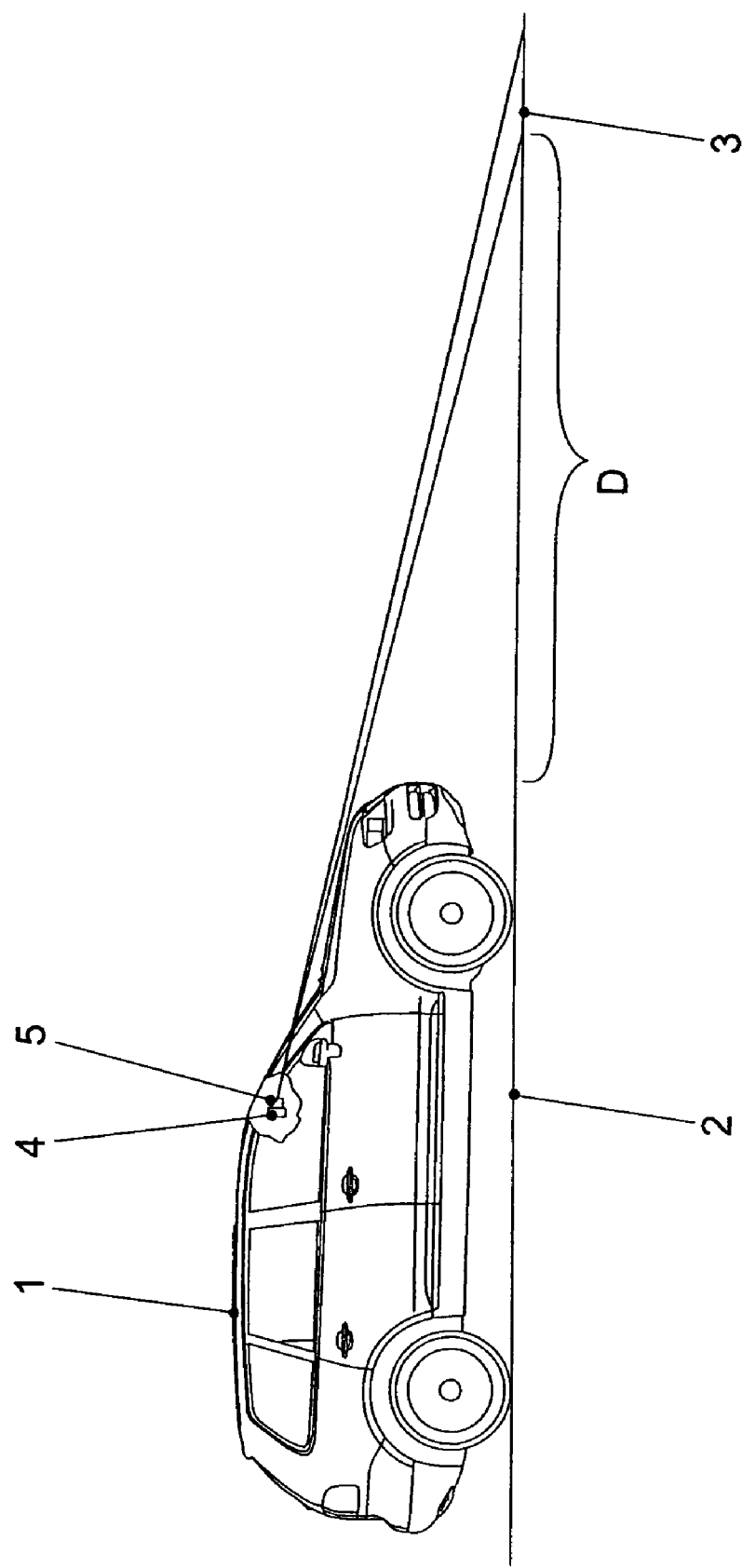
FIG. 1 shows a practical example of a vehicle with a device for determination of the surface condition of a roadway.

FIG. 1 shows a practical example of a vehicle 1 with a device 5 for determination of the surface condition of a roadway 2, on which vehicle 1 is traveling. In the present practical example, the device 5 for determination of the surface condition of the roadway 2 is arranged in the region of a rearview mirror 4. However, other positions can also be prescribed, for example, arrangement in a headlight. In the present practical example, it is prescribed that determination of the surface condition of the roadway 2 occurs for a region 3 of roadway 2 that lies at a distance D of about 5 m to 40 m in front of the vehicle 1. It can also be prescribed that the distance D is about 2 m to 200 m. In an advantageous embodiment, the distance D, during operation of vehicle 1, is adjusted as a function of speed of the vehicle 1. In another embodiment, the distance D, during, operation of vehicle 1, is adjusted above a limit speed in proportion to the speed of the vehicle 1.

Figure 2:
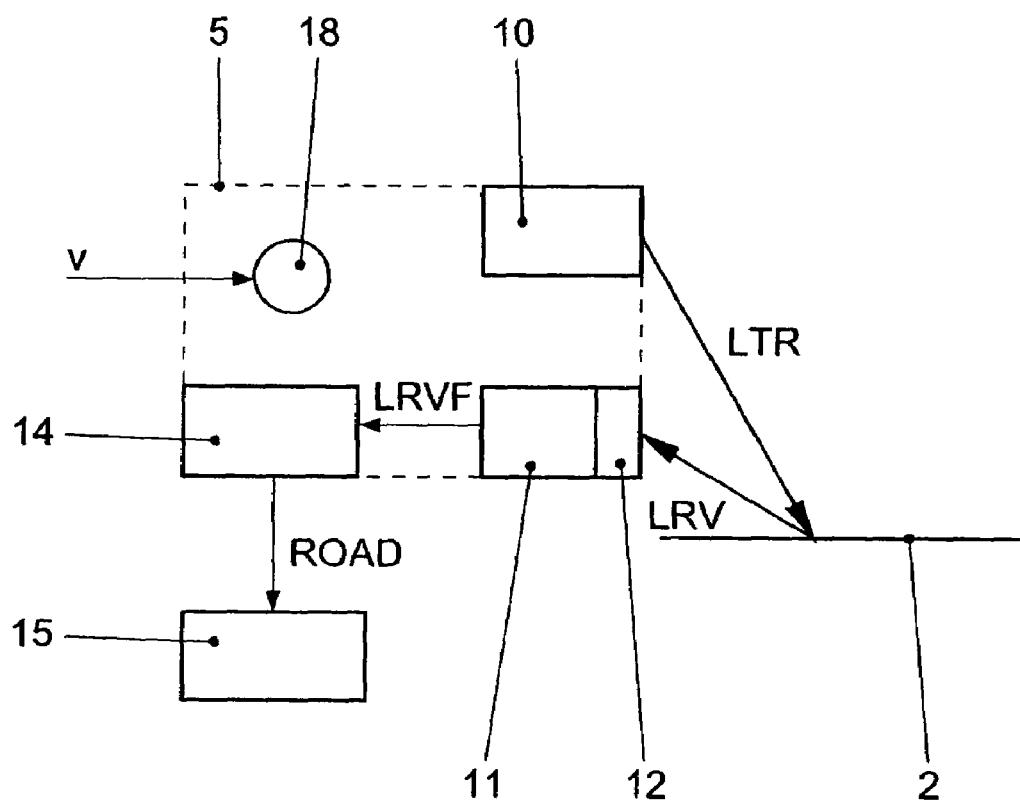
FIG. 2 shows a practical example of a device for determination of the surface condition of a roadway.

FIG. 2 shows a practical example of the device 5 for determination of the surface condition of a roadway 2. The device 5 for determination of the surface condition of roadway 2 includes an infrared emitter 10 to emit an infrared radiation LTR onto roadway 2, as well as a light-sensitive sensor 11 to measure a light signal LRV reflected from the roadway surface 2, and to emit a corresponding measurement signal that is subsequently designated filtered light signal LRVF. The infrared emitter 10 can also be emitted and/or replaced in its function by a headlight that is present anyway.

Figure 3:
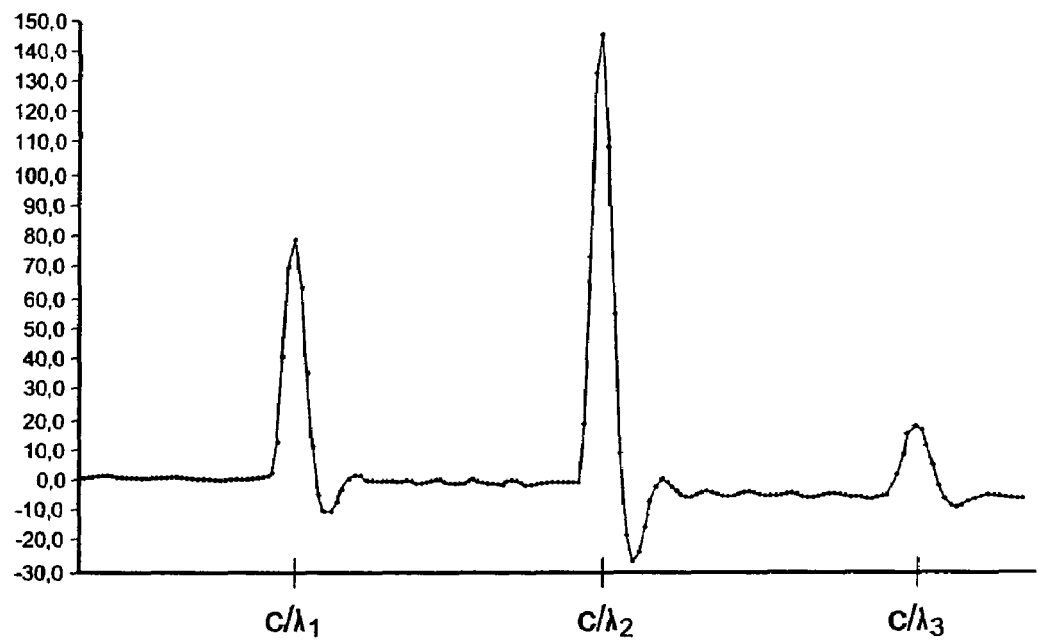
FIG. 3 shows a practical example of the power of a reflected and filtered light signal from an ice-covered roadway.
Figure 4:
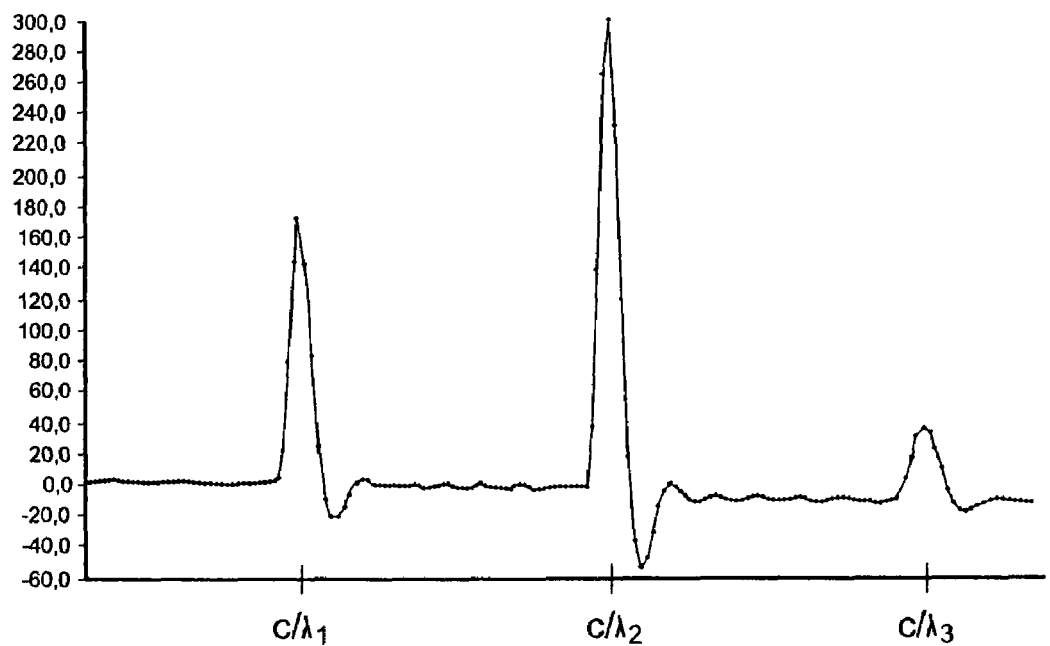
FIG. 4 shows a practical example of the power of a reflected and filtered light signal from a snow-covered roadway.

An optical filter 12 is arranged in front of the light-sensitive sensor 11, which allows light to pass through in a range around a first wavelength of 905 nm, in a range around a second wavelength of 850 nm and in a range around a third wavelength of 780 nm. FIG. 3 shows a corresponding practical example of a spectrum of the power of the reflected and filtered light signal LRVF from an ice-covered roadway, and FIG. 4 shows a practical example of a power spectrum of a reflected and filtered light signals LRVF from a snow-covered roadway, in which $\lambda_1$ denotes the first wavelength, $\lambda_2$ the second wavelength, $\lambda_3$ the third wavelength and c the speed of light.

The practical example of the device 5 for determination of the surface condition of the roadway 2 depicted in FIG. 2 also includes an analyzer 14 to determine the surface condition of roadway 2, and to emit a corresponding roadway condition indication ROAD. Determination of the surface condition of roadway 2 then occurs as a function of the power of the light signal LRV or LRVF at the first wavelength $\lambda_1$, at the second wavelength $\lambda_2$ and at least the third wavelength $\lambda_3$.

The infrared emitter 10, the light-sensitive sensor 11 and the analyzer 14 can be arranged in a housing or separately.

Instead of optical filter 12 in front of the light-sensitive sensor, it can also be prescribed that, by means of infrared emitter 10, essentially only light of a first wavelength $\lambda_1$, second wavelength $\lambda_2$ and third wavelength $\lambda_3$ is emitted.

The practical example of the device 5 for determination of surface condition of roadway 2 depicted in FIG. 2 also includes an actuator 18 to align the device 5 for determination of the surface condition of a roadway 2 as a function of the speed v of the vehicle 1 and therefore to achieve the desired distance D.

The roadway condition indication ROAD is intended for a sink 15, which can include, for example, a display to display the surface condition of roadway 2, like "ICE", "WET CONDITION", "SNOW", "SLIPPERY", "DANGER", etc., and/or an acoustic output of the surface condition of the roadway 2. As an alternative or in addition, the sink 15 also includes devices, like pneumatic spring adaption, tire pressure adaption, off-road recognition, road disturbance detection, active vibration control, automatic braking, an ABS (anti-locking system), an ESP (electronic stability program) and similar systems, an ASR (anti-skid control), an EDS, and FZR, an ANB (emergency brake), a μ-ump recognition (recognition of an abrupt or rapid change in friction coefficient) and/or an aquaplaning warning. The roadway condition indication ROAD can include a value for the friction coefficient and/or a condition statement, like "ice on the roadway", "snow on the roadway", "wet roadway" or "dry roadway".

The surface condition of roadway 2 can be determined by means of analyzer 14 as a function of the ratio $P\lambda_1/P\lambda_2$ with a power $P\lambda_1$ of light signal LRV or LRVF at the first wavelength $\lambda_1$ to the power $P\lambda_2$ of the light signal LRV or LRVF at the second wavelength $\lambda_2$, and as a function of the power $P\lambda_1$ (not in a ratio) of the light signal LRV or LRVF at the first wavelength $\lambda_1$, the power $P\lambda_2$ (not in a ratio) of the light signal LRV or LRVF at the second wavelength $\lambda_2$, and the power $P\lambda_3$ (not in a ratio) of the light signal LRV or LRVF at the third wavelength $\lambda_3$.

In the present practical example, it is prescribed that the surface condition of roadway 2 is determined by the analyzer 14 as function of the ratio $P\lambda_1/P\lambda_2$ of the power $P\lambda_1$ of light signal LRV or LRVF at the first wavelength $\lambda_1$ to the power $P\lambda_2$ of the light signal LRV or LRVF at the second wavelength $\lambda_2$, and as a function of the ratio $P\lambda_1/P\lambda_2$ of the power $P\lambda_1$ of the light signal LRV or LRVF at the first wavelength $\lambda_1$ to the power $P\lambda_3$ of the light signal LRV or LRVF at the third wavelength $\lambda_3$, and as a function of the ratio $P\lambda_3/P\lambda_2$ of the power $P\lambda_3$ of the light signal LRV or LRVF at the third wavelength $\lambda_3$ to the power $P\lambda_2$ of the light signal LRV or LRVF at the second wavelength $\lambda_2$ and as a function of the power $P\lambda_1$ (not in a ratio) of the light signal LRV or LRVF at the first wavelength $\lambda_1$, the power $P\lambda_2$ (not in a ratio) of the light signal LRV or LRVF at the second wavelength $\lambda_2$, and the power $P\lambda_3$ (not in a ratio) of the light signal LRV or LRVF at the third wavelength $\lambda_3$. The analyzer 14 can then be implemented as look-up table or as a neuronal net, as shown in the embodiment of FIG. 5.

Figure 5:
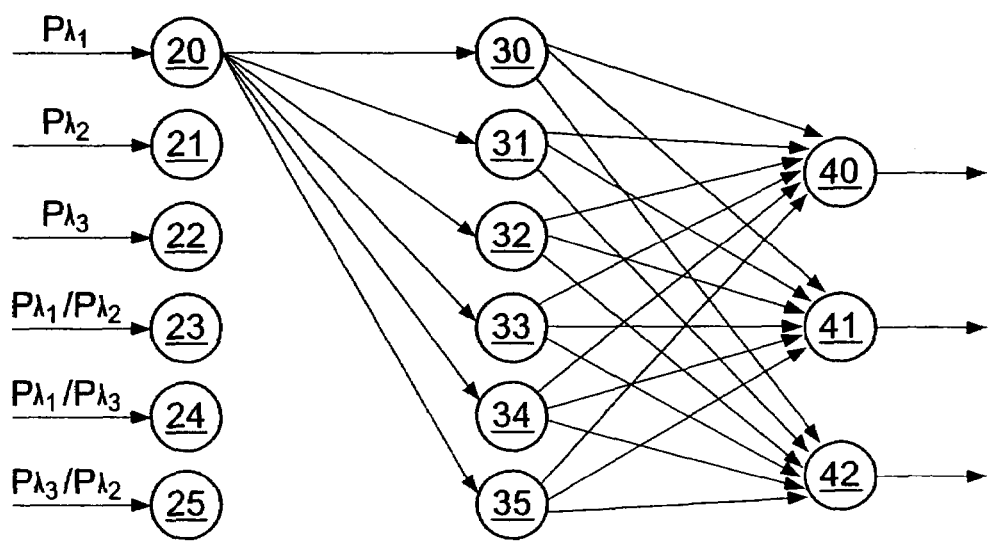
FIG. 5 shows a practical example of an analyzer, implemented by means of a neuronal net.

The neuronal net depicted in FIG. 5 includes six input nodes, 20, 21, 22, 23, 24, 25, six masked nodes 30, 31, 32, 33, 34, 35 and three output nodes 40, 41, 42, in which each input node 20, 21, 22, 23, 24, 25 is connected to each masked node 30, 31, 32, 33, 34, 35 (not all connections are shown in FIG. 5, for reasons of clarity), and each masked node 30, 31, 32, 33, 34, 35 is connected to each output node 40, 41, 42.

The input quantity in the input node 20 is the power $P\lambda_1$ of the light signal LRV or LRVF at the first wavelength $\lambda_1$, the input quantity in the input node 21 is the power $P\lambda_2$ of the light signal LRV or LRVF at the second wavelength $\lambda_2$, the input quantity in the input node 22 is the power $P\lambda_3$ of the light signal LRV or LRVF at the third wavelength $\lambda_3$, the input quantity in the input node 23 is the ratio $P\lambda_1/P\lambda_2$ with a power $P\lambda_1$ of light signal LRV or LRVF at the first wavelength $\lambda_1$ to the power $P\lambda_2$ of the light signal LRV or LRVF at the second wavelength $\lambda_2$, the input quantity of the input node 24 is the ratio $P\lambda 1/P\lambda_3$ of the power $P\lambda_1$ of the light signal LRV or LRVF at the first wavelength $\lambda_1$ to the power $P\lambda_3$ of the light signal LRV or LRVF at the third wavelength $\lambda_3$ and the input quantity of the input node 25 is the ratio $P\lambda_3/P\lambda_2$ of the power $P\lambda_3$ of the light signal LRV or LRVF at the third wavelength $\lambda_3$ to the power $P\lambda_2$ of the light signal LRV or LRVF at the second wavelength $\lambda_2$.

In the present practical example, it is prescribed that the output nodes 40, 41, 42 produce binary output quantities, in which the output quantity of the output node 40 is, 1', if the neuronal net recognizes an ice-covered roadway and otherwise, 0', in which the output quantity of the output node 40 is, 1', when the neuronal net recognizes a wet roadway and otherwise, 0', and in which the output quantity of the output node 42 is, 1', when the neuronal net recognizes a dry roadway and otherwise, 0'. More than three output nodes can also be prescribed, for example, for an iced roadway, for a snow-covered roadway, for a wet roadway, for a dirty roadway, for fog, for poor or absent roadway and/or for dry roadway. A single output node can also be prescribed, which furnishes as output quantity a value for the recognized friction coefficient of roadway 2. In the present case, for systems that process a value of a friction coefficient of roadway as input quantity, it is prescribed that the aforementioned conditions are converted to friction coefficients of the roadway 2. In this case, "iced roadway" is converted to a friction coefficient of $\mu=0.1$, "wet roadway" is converted to a friction coefficient of $\mu=0.4$ and "dry roadway" is converted to a friction coefficient of $\mu=0.8$.

Figure 6:
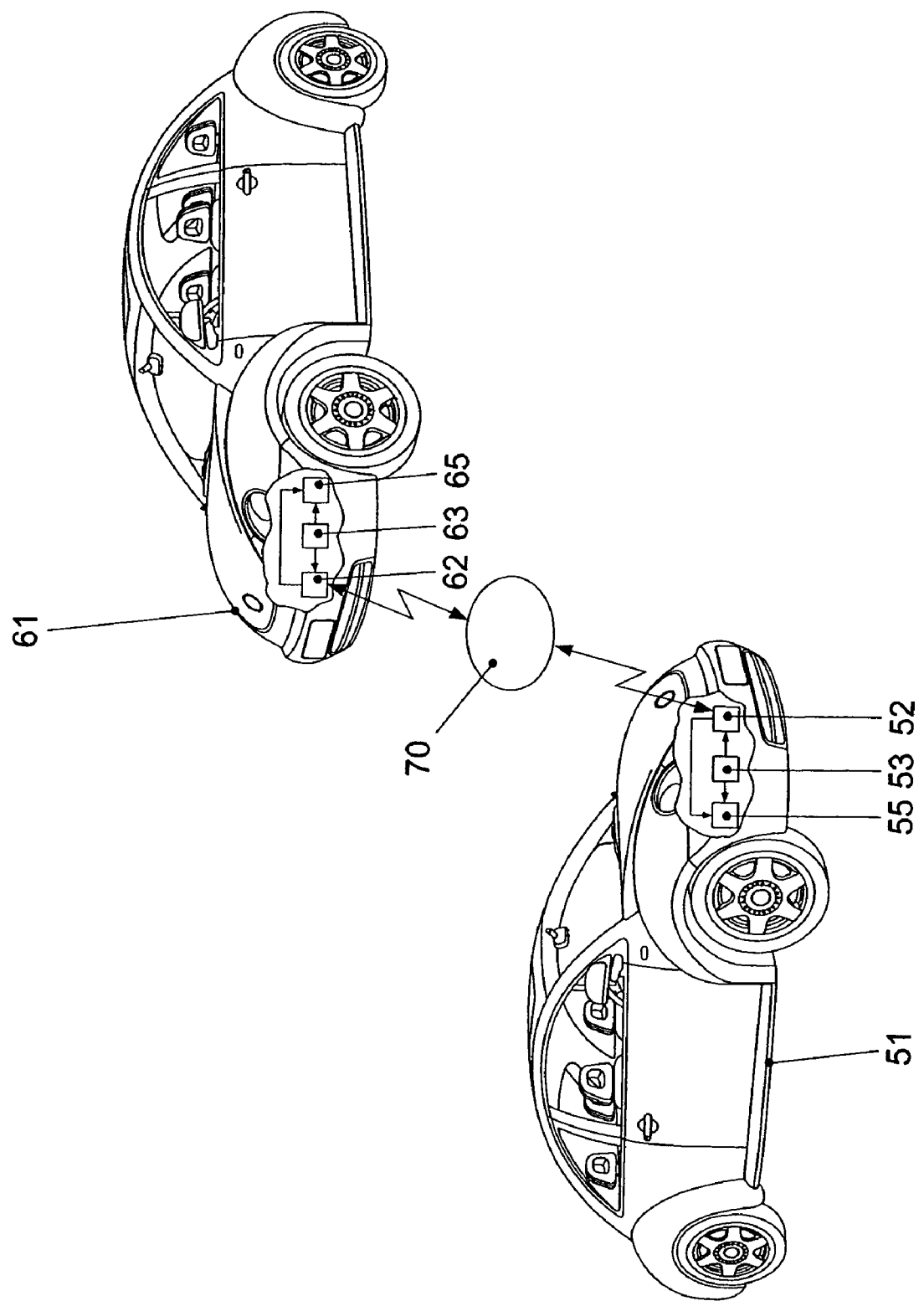
FIG. 6 shows a practical example of a transport system.

FIG. 6 shows a practical example of a transport system, in which the transport system includes at least a first vehicle 51 with the device 53 for determination of the surface condition of a roadway, and with a transmitter 52 to transmit information concerning the surface condition of the roadway, and at least a second vehicle 61 with a receiver 62 to receive the information concerning the surface condition of the roadway. Such a receiver 62 can be simply a radio or a receiver connected to a display to receive information sent from an exchange concerning a roadway condition, in which the information concerning the roadway condition is transmitted beforehand from the first vehicle 51 to a radio transmitter or to the exchange.

In the present practical example of a transport system, the first vehicle 51 includes a device 55 for determination of the surface condition of a roadway 2, a corresponding device 53 to determine the surface condition of a first roadway and a sink 55, corresponding to sink 15, and the second vehicle 61 includes a device 63 for determination of the surface condition of a second roadway, corresponding to the device 5 for determination of a surface condition of the roadway 2, and a sink 65, corresponding to sink 15. The first vehicle 51 also includes a transmitting and receiving device 52 to transmit information concerning the surface condition of the first roadway and to receive information concerning the surface condition of the second roadway. The second vehicle 61 also includes a transmitting and receiving device 62 to transmit information concerning the surface condition of the second roadway and to receive information concerning the surface condition of the first roadway. Communication between the first vehicle 61 and the second vehicle 62 occurs in the present practical example via an exchange 70.

The arrangement and size of the devices 53, 63, sinks 55, 65 and the transmitting and receiving devices 52, 62 in the vehicles 51, 61 in FIG. 6 are only to be understood in principle and do not depict the actual arrangement and size.

LIST OF REFERENCE NUMBERS

1, 51, 61 Vehicle
2 Roadway
3 Range
4 Rearview mirror
5, 53, 63 Device for determination of the surface condition of a roadway
10 Infrared emitter
11 Light-sensitive sensor
12 Optical filter
14 Analyzer
15, 55, 65 Sink
18 Actuator
20, 21, 22,
23, 24, 25 Input node
30, 31, 32,
33, 34, 35 Masked node
40, 41, 42 Output node
52, 62 Transmitting and receiving device
70 Exchange
D Distance
LRVF Filtered light signal
LRV Light signal
LTR Infrared radiation
$P\lambda_1$, $P\lambda_2$, $P\lambda_3$ Power
ROAD Roadway condition indication
v Speed
$\lambda_1$, $\lambda_2$, $\lambda_3$ Wavelength

The invention claimed is:

1. A device for determination of the surface condition of a roadway, the device comprising:
   a light-sensitive sensor to measure a light signal reflected from the surface of the roadway; and
   an analyzer to determine the surface condition of the roadway as a function of the power of the light signal at a first wavelength in the infrared range, at a second wavelength in the infrared range, and at least a third wavelength in the infrared range, wherein the device is operable to determine the surface condition of the roadway by means of the analyzer as a function of the ratio of the power of the light signal at the first wavelength to the power of the light signal at the second wavelength, as a function of the power of the light signal at the first wavelength, as a function of the power of the light signal at the second wavelength, and as a function of the power of the light signal at the third wavelength.

2. A device according to claim 1, wherein the first wavelength lies in a range between 950 nm and 850 nm.

3. A device according to claim 1, wherein the second wavelength lies in a range between 900 nm and 800 nm.

4. A device according to claim 1, wherein the third wavelength lies in a range between 850 nm and 750 nm.

5. A device according to claim 1, wherein the device is operable to determine the surface condition of the roadway by means of the analyzer as a function of the ratio of the power of the light signal at less than ten different wavelengths.

6. A vehicle, comprising a device according to claim 1, wherein the light-sensitive sensor is operable to measure the light signal reflected from the surface of the roadway at a distance in front of the vehicle, adjustable as a function of the speed of the vehicle.

7. A vehicle, comprising a device according to claim 1, wherein the light-sensitive sensor is operable to measure the light signal reflected from the surface of the roadway at a distance in front of the vehicle, adjustable in proportion to the speed of the vehicle.

8. A transport system, the transport system comprising:
   a first vehicle with a device to determine a surface condition of a roadway according to claim 1, further comprising a transmitter to transmit information concerning the surface condition of the roadway; and
   at least a second vehicle with a receiver to receive the information concerning the surface condition of the roadway.

9. A transport system according to claim 8, the second vehicle also comprising:
   a device to determine the surface condition of the roadway and a transmitter to transmit information concerning the surface condition of the roadway.

10. A transport system according to claim 9, the first vehicle also comprising:
    a receiver to receive the information transmitted from the second vehicle concerning the surface condition of the roadway.

11. A transport system according to claim 8, the second vehicle also comprising:
    a display to display the surface condition of the roadway.

12. A device for determination of the surface condition of a roadway, the device comprising:
    a light-sensitive sensor to measure a light signal reflected from the surface of the roadway; and
    an analyzer to determine the surface condition of the roadway as a function of the power of the light signal at a first wavelength in the infrared range, at a second wavelength in the infrared range, and at least a third wavelength in the infrared range, wherein the device is operable to determine the surface condition of the roadway by means of the analyzer as a function of the ratio of the power of the light signal at the first wavelength to the power of the light signal at the second wavelength, as a function of the ratio of the power of the light signal at the first wavelength to the power of the light signal at the third wavelength, and as a function of the ratio of the power of the light signal at the third wavelength to the power of the light signal at the second wavelength.

13. A device according to claim 12, wherein the first wavelength lies in a range between 950 nm and 850 nm.

14. A device according to claim 12, wherein the second wavelength lies in a range between 900 nm and 800 nm.

15. A device according to claim 12, wherein the third wavelength lies in a range between 850 nm and 750 nm.

16. A device according to claim 12, wherein the device is operable to determine the surface condition of the roadway by means of the analyzer as a function of the ratio of the power of the light signal at less than ten different wavelengths.

17. A vehicle, comprising a device according to claim 12, wherein the light-sensitive sensor is operable to measure the light signal reflected from the surface of the roadway at a distance in front of the vehicle, adjustable as a function of the speed of the vehicle.

18. A vehicle, comprising a device according to claim 12, wherein the light-sensitive sensor is operable to measure the light signal reflected from the surface of the roadway at a distance in front of the vehicle, adjustable in proportion to the speed of the vehicle.

19. A device for determination of the surface condition of a roadway, the device comprising:
   a light-sensitive sensor to measure a light signal reflected from the surface of the roadway; and
   an analyzer that determines the surface condition of the roadway, wherein the determination is made using a function of the power of the light signal at a first wavelength in the infrared range, a second wavelength in the infrared range, and a third wavelength in the infrared range, as well as a function of the ratio of the power of the light signal at the first wavelength to the power of the light signal at the second wavelength.

20. A device according to claim 19, wherein the first wavelength lies in the range between 950 nm and 800 nm.

21. A device according to claim 19, wherein the second wavelength lies in the range between 900 nm and 750 nm.

22. A device according to claim 19, wherein the device is operable to determine the surface condition of the roadway by means of the analyzer as a function of the ratio of the power of the light signal at less than ten different wavelengths.

23. A vehicle, comprising a device according to claim 19, wherein the light-sensitive sensor is operable to measure the light signal reflected from the surface of the roadway at a distance in front of the vehicle, adjustable as a function of speed of the vehicle.

24. A vehicle, comprising a device according to claim 19, wherein the light-sensitive sensor is operable to measure the light signal reflected from the surface of the roadway at a distance in front of the vehicle, adjustable in proportion to the speed of the vehicle.

* * * * *